United States Patent
Wang et al.

(10) Patent No.: US 8,741,176 B2
(45) Date of Patent: Jun. 3, 2014

(54) LIQUID CRYSTAL COMPOUND

(75) Inventors: Chun-Chih Wang, Taichung (TW); Chin-Yen Chang, Pingtung County (TW); Yu-Ying Hsieh, Kaohsiung (TW)

(73) Assignee: Daxin Materials Corporation, Taichung (TW)

( * ) Notice: Subject to any disclaimer, the term of this patent is extended or adjusted under 35 U.S.C. 154(b) by 112 days.

(21) Appl. No.: 13/415,860

(22) Filed: Mar. 9, 2012

(65) Prior Publication Data

US 2012/0264984 A1    Oct. 18, 2012

(30) Foreign Application Priority Data

Apr. 18, 2011    (TW) .............................. 100113396 A

(51) Int. Cl.
    C09K 19/12    (2006.01)
    C09K 19/32    (2006.01)
    C09K 19/30    (2006.01)
    C07C 25/18    (2006.01)

(52) U.S. Cl.
    USPC ................... 252/299.62; 252/299.63; 560/81; 568/325; 568/579; 570/127

(58) Field of Classification Search
    None
    See application file for complete search history.

(56) References Cited

U.S. PATENT DOCUMENTS

| | | | |
|---|---|---|---|
| 4,873,019 A | 10/1989 | Krause et al. | |
| 7,390,538 B2 | 6/2008 | Manabe et al. | |
| 2011/0043747 A1* | 2/2011 | Kawasaki et al. | 349/186 |
| 2012/0181479 A1* | 7/2012 | Furusato et al. | 252/299.61 |
| 2013/0119312 A1* | 5/2013 | Wittek et al. | 252/299.61 |

FOREIGN PATENT DOCUMENTS

| | | |
|---|---|---|
| EP | 0132377 | 1/1985 |
| WO | 2009100204 | 8/2009 |
| WO | WO 2009100204 A1 * | 8/2009 |

* cited by examiner

*Primary Examiner* — Jafar Parsa
*Assistant Examiner* — Medhanit Bahta
(74) *Attorney, Agent, or Firm* — Jianq Chyun IP Office

(57) ABSTRACT

A liquid crystal compound with high optical anisotropy is provided. The liquid crystal compound is represented by formula (I),

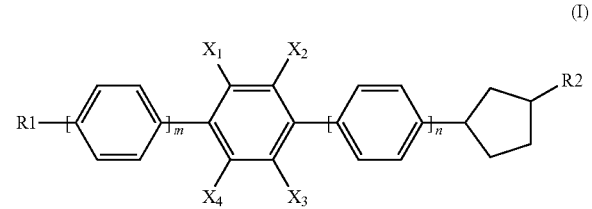

wherein each of R1 and R2 represents an alkyl group having 1 to 10 carbon atoms or an alkenyl group having 2 to 10 carbon atoms; the alkyl group and the alkenyl group are unsubstituted or substituted by —O—, —CO—, or —COO— groups; each of $X_1$, $X_2$, $X_3$, and $X_4$ represents hydrogen or fluorine, and at least one of $X_1$, $X_2$, $X_3$, and $X_4$ is fluorine; m is 1, 2, or 3; n is 0, 1, or 2, and $2 \leq m+n \leq 3$.

5 Claims, No Drawings

LIQUID CRYSTAL COMPOUND

CROSS-REFERENCE TO RELATED APPLICATION

This application claims the priority benefit of Taiwan application serial no. 100113396, filed Apr. 18, 2011. The entirety of the above-mentioned patent application is hereby incorporated by reference herein and made a part of this specification.

BACKGROUND OF THE INVENTION

1. Field of the Invention

The present invention is related to a liquid crystal compound, and in particular to a liquid crystal compound having a low nematic phase floor temperature and high optical anisotropy.

2. Description of Related Art

In order to enhance characteristics of a liquid crystal display device, a liquid crystal composition used by the device must have suitable properties. The liquid crystal composition usually includes a plurality of liquid crystal compounds, and each of the liquid crystal compounds has one or a plurality of the following properties: stable chemical and physical properties; having a high clearing point (a liquid crystal phase—isotropic phase transformation temperature); a low liquid crystal phase (nematic phase, smectic phase, etc.) floor temperature, especially a low nematic phase floor temperature; low viscosity; having suitable optical anisotropy; having suitable dielectric constant anisotropy; and superb compatibility with other liquid crystal compounds.

By using the composition which includes the liquid crystal compound with stable chemical and physical properties in the display device, the voltage holding ratio of the liquid crystal composition is enhanced.

By using the composition which includes the liquid crystal compound with a high clearing point and a low liquid crystal phase floor temperature, the nematic phase temperature range of the liquid crystal composition is expanded, so that the display device is able to be used in a wide temperature range.

Moreover, by using the composition which includes the compound with low viscosity in the display device, the response speed of the liquid crystal composition is increased; by using the composition which includes the compound with suitable optical anisotropy in the display device, the contrast of the display device is increased.

When developing a liquid crystal material of optical anisotropy, birefringence is able to be increased by increasing conjugated structures on the long molecular axis. Generally, a structure with at least three benzene rings is required for Δn to have a chance to be greater than 0.2. However, a liquid crystal compound which includes the structure with at least three benzene rings makes the nematic phase floor temperature increase, thereby reducing the temperature range in which the liquid crystal compound may be used.

SUMMARY OF THE INVENTION

The present invention provides a liquid crystal compound having a low nematic phase floor temperature and high optical anisotropy, so as to expand an applicable range of the liquid crystal compound.

The present invention provides a liquid crystal compound with high optical anisotropy. The liquid crystal compound is represented by formula (I),

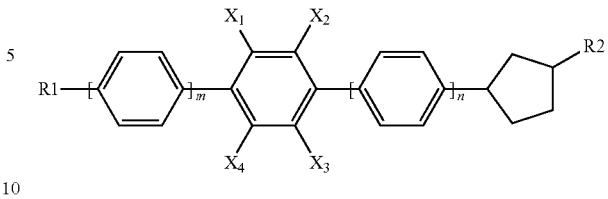

(I)

wherein each of R1 and R2 represents an alkyl group having 1 to 10 carbon atoms or an alkenyl group having 2 to 10 carbon atoms; the alkyl group and the alkenyl group are unsubstituted or substituted by —O—, —CO—, or —COO— groups; each of $X_1$, $X_2$, $X_3$, and $X_4$ represents hydrogen or fluorine, and at least one of $X_1$, $X_2$, $X_3$, and $X_4$ is fluorine; m is 1, 2, or 3; n is 0, 1, or 2, and 2≤m+n≤3.

According to an embodiment of the present invention, in formula (I), $X_1$ is F, and $X_2$, $X_3$, and $X_4$ are H.

According to an embodiment of the present invention, in formula (I), $X_2$ is F, and $X_1$, $X_3$, and $X_4$ are H.

According to an embodiment of the present invention, in formula (I), $X_1$ and $X_3$ are F, and $X_2$ and $X_4$ are H.

According to an embodiment of the present invention, in formula (I), R2 is a propyl group, a butyl group, or an amyl group.

In light of the above, the liquid crystal compound according to the present invention has a low nematic phase floor temperature and high optical anisotropy, which are advantageous to subsequent applications and development of the liquid crystal compound.

In order to make the aforementioned and other objects, features and advantages of the present invention comprehensible, embodiments accompanied with figures are described in detail below.

DETAILED DESCRIPTION OF DISCLOSED EMBODIMENTS

The following describes the compound further in concrete detail.

The compound according to the disclosure is a compound represented by formula (I).

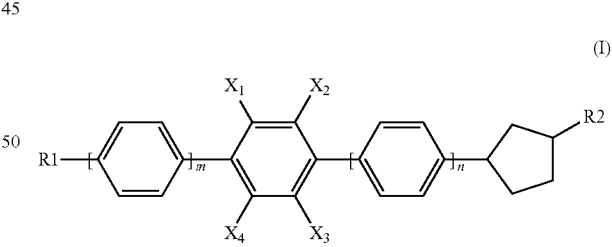

(I)

In formula (I), each of R1 and R2 represents an alkyl group having 1 to 10 carbon atoms or an alkenyl group having 2 to 10 carbon atoms; the alkyl group and the alkenyl group are unsubstituted or substituted by —O—, —CO—, or —COO— groups.

The alkyl group may be, for example, a methyl group, an ethyl group, a propyl group, an isopropyl group, a butyl group, a tert-butyl group, an amyl group, a hexyl group, a heptyl group, an octyl group, a nonyl group, or a decyl group.

The alkenyl group may be an unsubstituted alkenyl group with 2 to 10 carbon atoms such as a vinyl group, an propenyl group, an isopropenyl group, a butenyl group, a pentenyl group, a hexenyl group, a heptenyl group, an octenyl group, a nonanyl group, or a decenyl group.

In formula (I), each of $X_1$, $X_2$, $X_3$, and $X_4$ is H or F, and at least one of $X_1$, $X_2$, $X_3$, and $X_4$ is F. For example, $X_1$ is F, $X_2$, $X_3$, and $X_4$ are H; $X_2$ is F, $X_1$, $X_3$, and $X_4$ are H; $X_3$ is F, $X_1$, $X_2$, and $X_4$ are H; or $X_4$ is F, $X_1$, $X_2$, and $X_3$ are H.

In formula (I), m is 1, 2, or 3; n is 0, 1, or 2, and $2 \leq m+n \leq 3$.

The compound in formula (I) may be a compound shown in the following formulae (I-1) to (I-5).

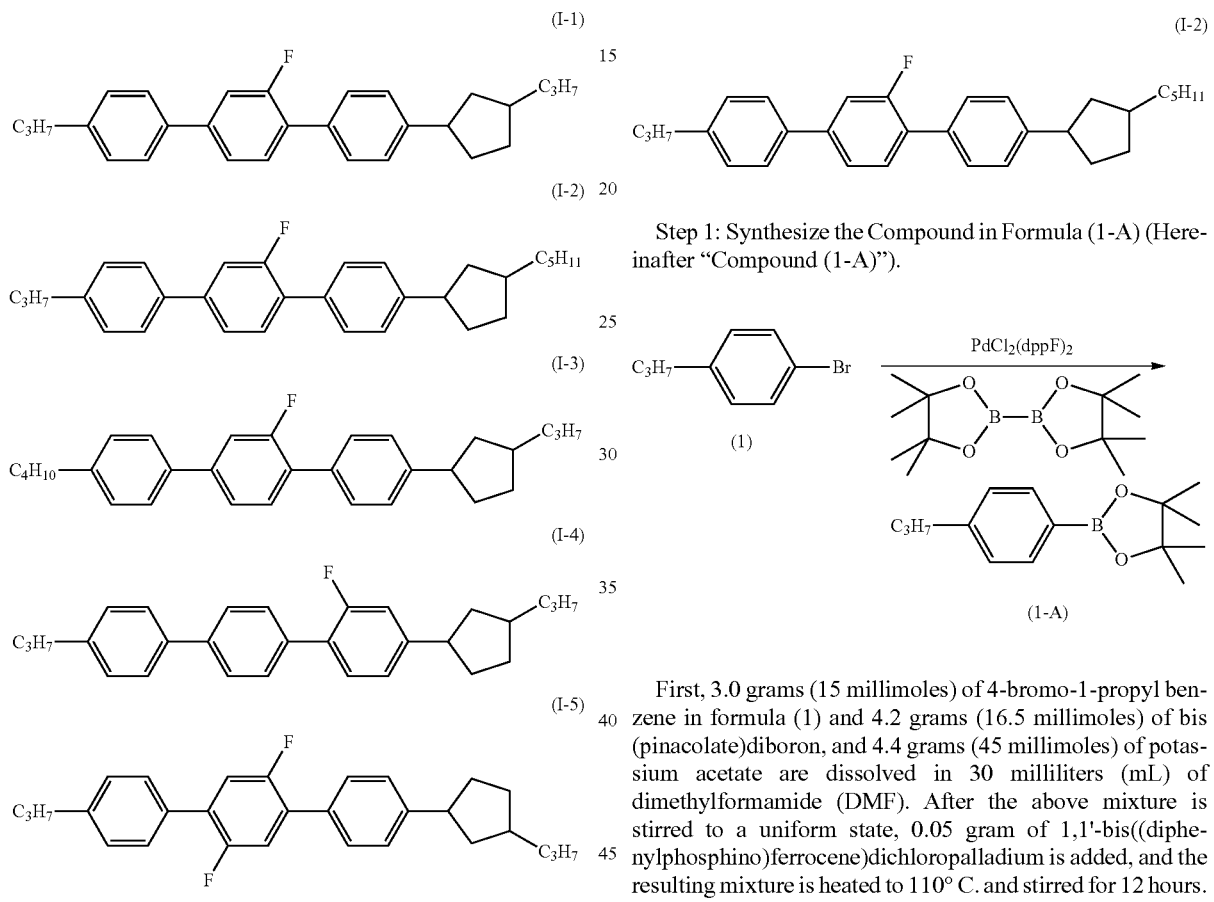

The liquid crystal compound according to the disclosure includes a structure with at least two benzene rings on a molecular main axis, so that the compound has high optical anisotropy and low viscosity. Also, the cyclopentylidenyl group in formula (I) is conjugated with an extension group R2, as shown in the following formula (II). Therefore, the structures of the liquid crystals are warped, so that the liquid crystal compounds have looser structures, thereby lowering a crystalline phase—nematic phase transformation temperature.

The following demonstrates the efficacy of the disclosure through experimental embodiment 1 to experimental embodiment 4 and comparative embodiment 1 to comparative embodiment 3.

Experimental Embodiment 1

Preparation of the Compound in Formula (I-2)

Step 1: Synthesize the Compound in Formula (1-A) (Hereinafter "Compound (1-A)").

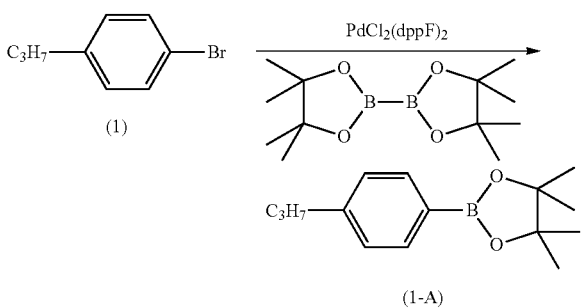

First, 3.0 grams (15 millimoles) of 4-bromo-1-propyl benzene in formula (1) and 4.2 grams (16.5 millimoles) of bis(pinacolate)diboron, and 4.4 grams (45 millimoles) of potassium acetate are dissolved in 30 milliliters (mL) of dimethylformamide (DMF). After the above mixture is stirred to a uniform state, 0.05 gram of 1,1'-bis((diphenylphosphino)ferrocene)dichloropalladium is added, and the resulting mixture is heated to 110° C. and stirred for 12 hours. After reacting, 50 mL of water is added to the mixture, and the mixture is extracted by ethyl acetate. An organic layer of the mixture solution is desiccated by waterless magnesium sulfate and is filtered and concentrated. Afterwards, column chromatography (silicone, hexane) is performed to purify the product, thereby obtaining 3.3 grams of a light yellow solid compound (1-A). The yield is 90%.

Step 2: Synthesize the Compound in Formula (1-B) (Hereinafter "Compound (1-B)").

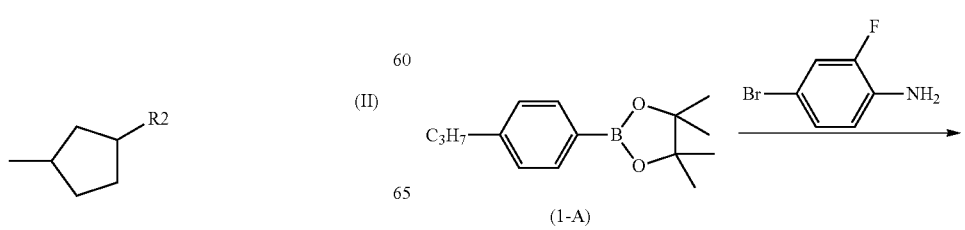

-continued

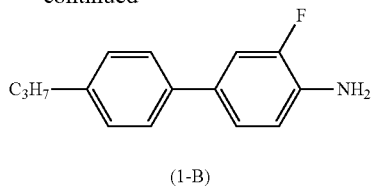

(1-B)

Next, 1.4 grams (5.8 millimoles) of the compound (1-A) and 1 gram (5.3 millimoles) of 4-bromo-2-fluoroaniline are dissolved in 20 mL of toluene. After the above mixture is stirred to a uniform state, 2.1 grams (15.8 millimoles) of potassium carbonate, 7 mL of water, and 0.5 mL of Aliquate™ 336 are added, and the resulting mixture reacts in an oxygen-depleted bottle for 1 hour. Then, 0.24 gram of Pd(PPh$_3$)$_4$ is added, and the resulting mixture is heated to 85° C. and stirred for 12 hours. The above mixture is diluted by ethyl acetate and extracted by water.

Afterwards, an organic layer of the above mixture solution is desiccated by waterless magnesium sulfate and is then filtered and concentrated. Column chromatography (silicone, ethyl acetate/hexane=¼) is performed to purify the product, thereby obtaining 0.9 gram of a light yellow solid compound (1-B). The yield is 75%.

Step 3: Synthesize the Compound in Formula (1-C) (Hereinafter "Compound (1-C)").

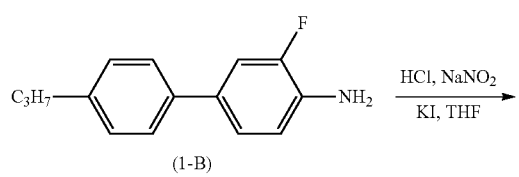

Next, 1.2 grams (5.2 millimoles) of the compound (1-B) is added to 2.6 mL of 35% hydrochloric acid and 20 mL of tetrahydrofuran (THF). After stirring the above mixture in an ice bath for 10 minutes, a sodium nitrite solution is slowly dripped into the mixture. This sodium nitrite solution is prepared by adding 0.7 gram (10.4 millimoles) of sodium nitrite into 2 mL of water. After stirring the above mixture in an ice bath for 10 minutes, a potassium iodide solution is slowly dripped into the mixture. This potassium iodide solution is prepared by adding 1.7 grams (10.4 millimoles) of potassium iodide into 5 mL of water. The above mixture solution is heated from 0° C. to room temperature and then stirred for 1 hour. After the above mixture solution completes reacting, a 10% sodium bicarbonate solution is added to the mixture until the mixture becomes neutral. Ethyl acetate and water are used for extraction, and an organic layer of the mixture solution is desiccated by waterless magnesium sulfate and is then filtered and concentrated. Column chromatography (silicone, hexane) is performed to purify the product, thereby obtaining 1.7 grams of a transparent liquid compound (1-C). The yield is 96%.

Step 4: Synthesize the Compound in Formula (1-D) (Hereinafter "Compound (1-D)").

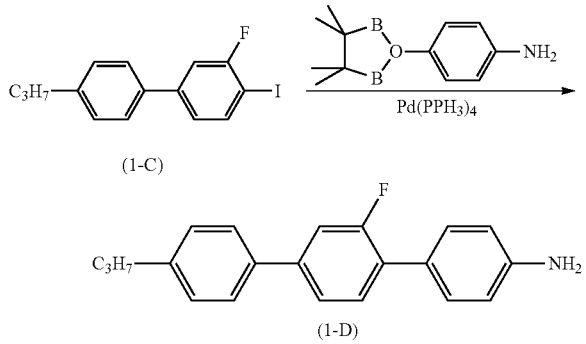

Next, 1 gram (2.9 millimoles) of the compound (1-C) and 0.63 gram (2.9 millimoles) of 4-aminophenyl boronic acid pinacol ester are dissolved in 15 mL of toluene. After the above mixture is stirred to a uniform state, 1.2 grams (8.7 millimoles) of potassium carbonate, 4 mL of water, and 0.1 mL of Aliquate™ 336 are added. After the resulting mixture reacts in an oxygen-depleted bottle for 1 hour, 0.16 gram of Pd(PPh$_3$)$_4$ is added, and the resulting mixture is heated to 85° C. and stirred for 12 hours. The above mixture is diluted by ethyl acetate and extracted by water. An organic layer of the mixture solution is desiccated by waterless magnesium sulfate and is filtered and concentrated. Afterwards, methanol and water are used to precipitate the above mixture solution, thereby obtaining 0.62 gram of a light yellow solid compound (1-D). The yield is 70%.

Step 5: Synthesize the Compound in Formula (1-E) (Hereinafter "Compound (1-E)").

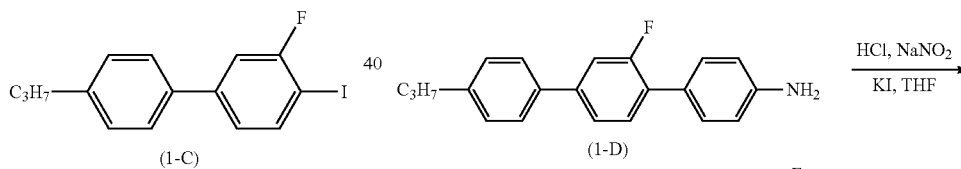

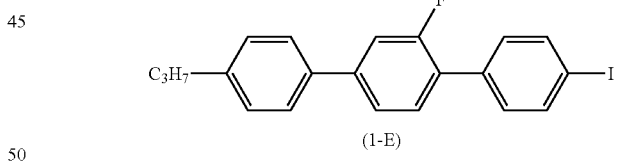

Next, 0.4 gram (1.3 millimoles) of the compound (1-D) is added to 0.4 mL of 35% hydrochloric acid and 10 mL of THF. After stirring the above mixture in an ice bath for 10 minutes, a sodium nitrite solution is slowly dripped into the mixture. This sodium nitrite solution is prepared by adding 0.18 gram (2.6 millimoles) of sodium nitrite into 0.7 mL of water. After stirring the above mixture in an ice bath for 10 minutes, a potassium iodide solution is slowly dripped into the mixture. This potassium iodide solution is prepared by adding 0.43 gram (2.6 millimoles) of potassium iodide into 2 mL of water. The above mixture solution is heated from 0° C. to room temperature and then stirred for 1 hour. After the above mixture completes reacting, a 10% sodium bicarbonate solution is added to the mixture until the mixture is neutral, and the mixture is extracted by ethyl acetate and water. Afterwards, an organic layer of the mixture solution is desiccated by waterless magnesium sulfate and is then filtered and concentrated, and column chromatography (silicone, hexane) is performed to purify the product, thereby obtaining 0.51 gram of a white solid compound (1-E). The yield is 94%.

Step 6: Synthesize the Compound in Formula (1-F) (Hereinafter "Compound (1-F)").

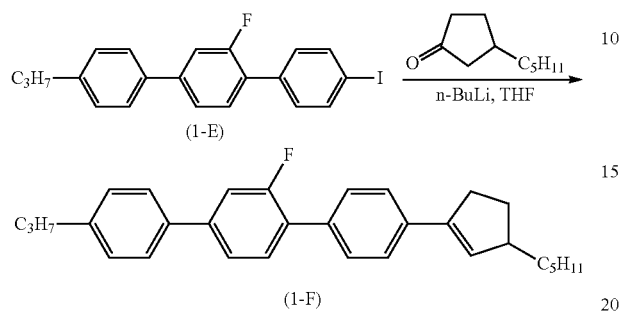

Next, 0.32 gram (0.77 millimole) of the compound (1-E) is dissolved in 5 mL of THF, and 0.34 mL (0.85 millimole) of 2.5 M n-BuLi is added at a temperature of −78° C. Then, after the above mixture solution is stirred for 30 minutes at a temperature of −78° C., 0.12 gram (0.77 millimole) of 3-pentylcyclopentanone is added. The above mixture solution is stirred, heated to room temperature, and is extracted by ethyl acetate and extracted by water. Afterwards, an organic layer of the mixture solution is desiccated by waterless magnesium sulfate and is then filtered and concentrated, and column chromatography (silicone, hexane) is performed to purify the product. The obtained initial product is added with $KHSO_4$ as a catalyst, is heated to 120° C. without any solvent, and reacts for 2 hours. After being cooled down, hexane is added to dilute the above reactant, and column chromatography (silicone, hexane) is performed to purify the product. 0.17 gram of a white solid compound (1-F) is obtained. The yield is 53%.

Step 7: Synthesize the Compound in Formula (I-2) (Hereinafter "Compound (I-2)").

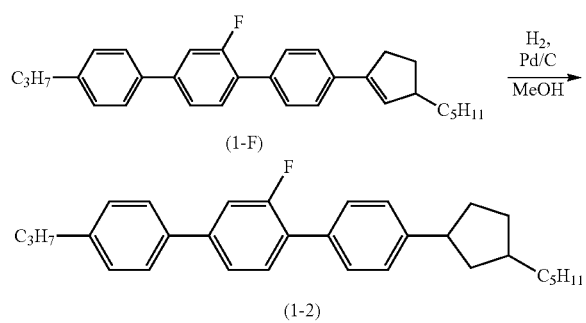

0.17 gram (0.4 millimole) of the compound (1-F) is added to 1 mL of toluene and 10 mL methanol. After 4 milligrams of 10% Pd—C is added, the above mixture solution is stirred in hydrogen for 8 hours. After aspirating a filtrate after filtration, 0.16 gram of a greasy compound (I-2) is obtained. The yield is 94%.

($^1$H NMR, $CDCl_3$, ppm) δ=0.80-0.89 (m, 6H), 1.05-1.48 (m, 7H), 1.48-1.55 (m, 2H), 1.73-2.23 (m, 4H), 2.59-2.64 (t, 2H), 3.03-3.07 (m, 1H), 7.26-7.29 (m, 2H), 7.32-7.38 (m, 2H), 7.41-7.44 (m, 2H), 7.45-7.48 (m, 1H), 7.48-7.50 (m, 2H), 7.50-7.58 (m, 4H).

Experimental Embodiment 2

Preparation of the Compound in Formula (I-4)

(I-4)

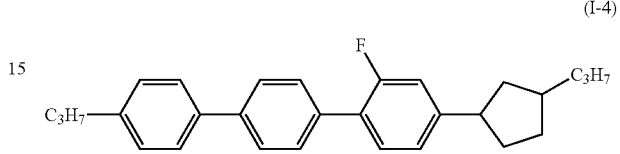

Step 1: Synthesize the Compound in Formula (2-A) (Hereinafter "Compound (2-A)").

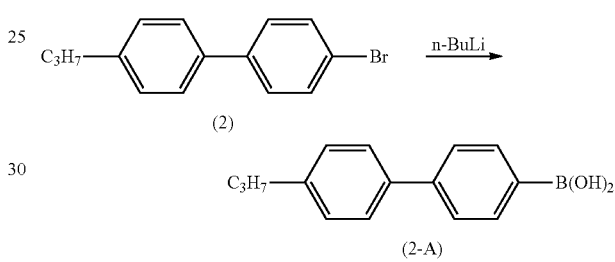

First, 10 grams of 4-bromo-1-propyl benzene in formula (2) is placed in a two-neck bottle. The two-neck bottle is heated, and waterless THF is injected into the two-neck bottle. After the two-neck bottle is cooled to −78° C., 18 mL of an n-BuLi solution is slowly dripped into the two-neck bottle. After maintaining the reaction temperature at −78° C. for 1 hour, 10 mL of 2-isopropoxy-4,4,5,5-tetramethyl-1,3,2-dioxaborolane is slowly dripped into the two-neck bottle. After continuing the reaction for 1 hour, the bottle is heated to room temperature. 10 mL of distilled water is added to the above double-neck bottle, and low pressure evaporation-concentration is performed to remove the THF. Ethyl acetate and distilled water are used to extract the obtained mixture solution. Afterwards, the collected organic solution is desiccated by waterless magnesium sulfate, and the solid magnesium sulfate is removed by gravitational filtration. Then, low pressure evaporation-concentration is performed on the obtained mixture solution to remove the solvent. 9.47 grams of a white solid compound (2-A) is obtained. The yield is 80%.

Step 2: Synthesize the Compound in Formula (2-B) (Hereinafter "Compound (2-B)").

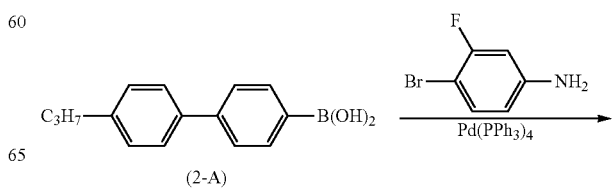

-continued

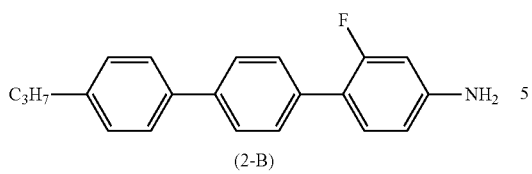
(2-B)

Next, 9.47 grams of the compound (2-A), 5.58 grams of 4-bromo-2-fluorobenzenamine, 12.2 grams of potassium carbonate, 30 mL of distilled water, 150 mL of toluene, and 0.5 mL Aliquate™ 336 which is used as a surfactant are placed in a 250 mL double-neck bottle. After heating the double-neck bottle until convection occurs, 0.5 mL of tetrakis(triphenylphosphine)palladium (0) which is used as a catalyst is added to the double-neck bottle. The bottle is heated for another 18 hours with convection. After the reaction is complete, the bottle is cooled to room temperature, and the mixture solution is extracted by ethyl acetate and distilled water. After all the collected organic solution is desiccated by waterless magnesium sulfate, gravitational filtration is performed to remove the solid magnesium sulfate, and low pressure evaporation-concentration is performed to remove the solvent. The obtained product is dissolved in 15 mL of dichloromethane, and 150 mL of hexane is used for further precipitation. Aspiration filtration is then performed to collect solid materials, thereby obtaining 7 grams of a yellow solid compound (2-B). The yield is 78%.

Step 3: Synthesize the Compound in Formula (2-C) (Hereinafter "Compound (2-C)").

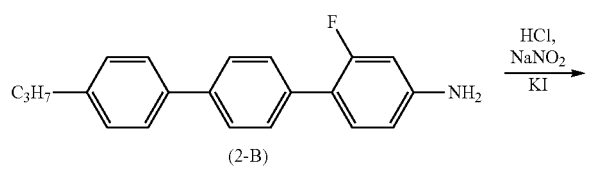

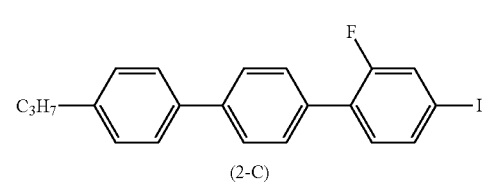
(2-C)

Next, 3 grams of the compound (2-B) is placed in a single-neck bottle, is dissolved in 30 mL of THF, and is chilled by an ice and salt bath to between 5° C. and −5° C. Next, 0.5 mL of sulfuric acid is slowly dripped into the single-neck bottle. After maintaining a low temperature for 10 minutes, 5 mL of a 2.9 M sodium nitrate solution is slowly dripped into the bottle, and after maintaining a low temperature for another 10 minutes, 5 mL of a 2.9 M potassium iodide solution is slowly dripped into the bottle, and after maintaining a low temperature for still another 1 hour, low pressure evaporation-concentration is performed to remove the solvent. Column chromatography with hexane as an eluent is performed to purify the product, thereby obtaining 1.5 grams of a white solid compound (2-C). The yield is 50%.

Step 4: Synthesize the Compound in Formula (2-D) (Hereinafter "Compound (2-D)").

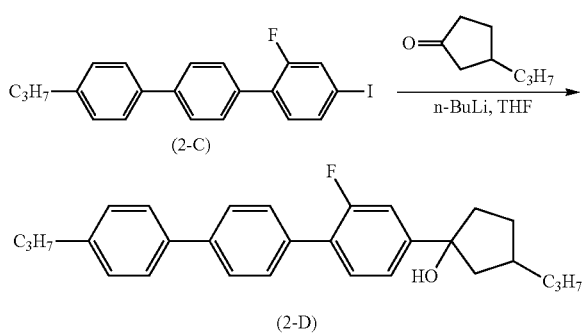

Then, 1.5 grams of the compound (2-C) is placed in a two-neck bottle. The two-neck bottle is heated, and waterless THF is injected into the two-neck bottle. After cooling the temperature of the bottle to −78° C., 2.6 mL of an n-BuLi solution is slowly dripped into the two-neck bottle. After maintaining the reaction at −78° C. for 1 hour, 0.45 mL of 3-propylcyclopentanone is slowly dripped into the bottle. The reaction is continued for 1 hour. Afterwards, the double-neck bottle is heated to room temperature, and 10 mL of distilled water is added to the bottle. Low pressure evaporation-concentration is performed to remove the THF, and the mixture solution is extracted by ethyl acetate and distilled water. After all the collected organic solution is desiccated by waterless magnesium sulfate, gravitational filtration is performed to remove the solid magnesium sulfate, and low pressure evaporation-concentration is performed to remove the solvent. Column chromatography with hexane as an eluent is performed to purify the obtained product, thereby obtaining 0.6 gram of a yellow liquid compound (2-D). The yield is 40%.

Step 5: Synthesize the Compound in Formula (2-E) (Hereinafter "Compound (2-E)").

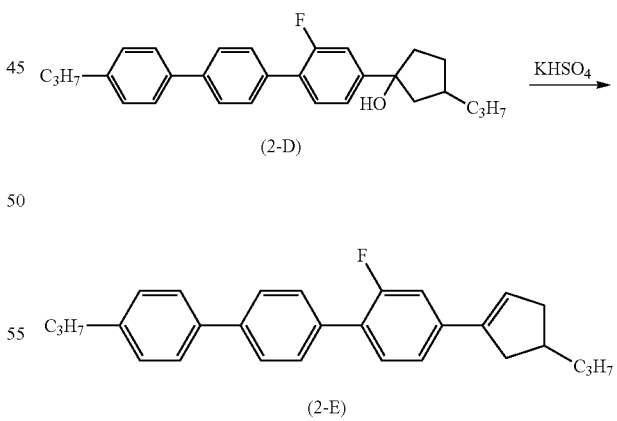

Next, 0.6 gram of the compound (2-D) and 1 gram of potassium hydrogen sulfate are placed in a 100 mL single-neck bottle, are heated to 120° C., and react for 4 hours. The product is taken from the single-neck bottle, and column chromatography with hexane as an eluent is performed to purify the product, thereby obtaining 0.55 gram of a white solid compound (2-E). The yield is 92%.

Step 6: Synthesize the Compound in Formula (I-4) (Hereinafter "Compound (I-4)").

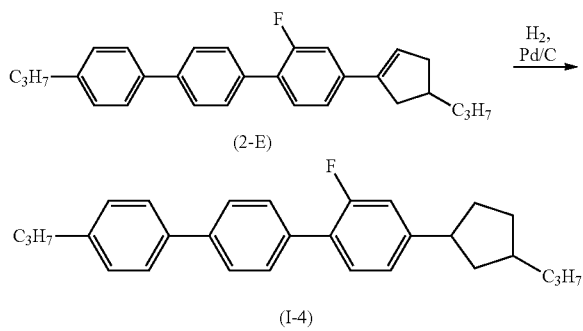

Last, 0.55 gram of the compound (2-E), 10 milligrams of Pd—C, 10 mL of ethanol, and 8 mL of toluene are placed in a 100 mL single-neck bottle. Hydrogen is channeled into the single-neck bottle at room temperature and reacts for 18 hours. Gravitational filtration is performed on the mixture solution to remove the Pd—C, and low pressure evaporation-concentration is performed to remove the solvent. Column chromatography with hexane as an eluent is performed to purify the obtained product, thereby obtaining 0.5 gram of a white solid compound (I-4). The yield is 99%.

($^1$H NMR, CDCl$_3$, ppm) δ=0.87-0.98 (m, 6H), 1.21-1.39 (m, 7H), 1.39-1.70 (m, 2H), 1.70-2.19 (m, 4H), 2.59-2.64 (t, 2H), 3.02-3.08 (m, 1H), 7.00-7.08 (m, 2H), 7.23-7.25 (d, 2H), 7.34-7.39 (t, 1H), 7.52-7.64 (m, 6H).

Experimental Embodiment 3

Preparation of the Compound in Formula (I-1)

Step 1: the Synthesis of the Compound (1-E) is Shown in Embodiment 1 the Compound in Formula (3-F) (Hereinafter "Compound (3-F)") is Synthesized.

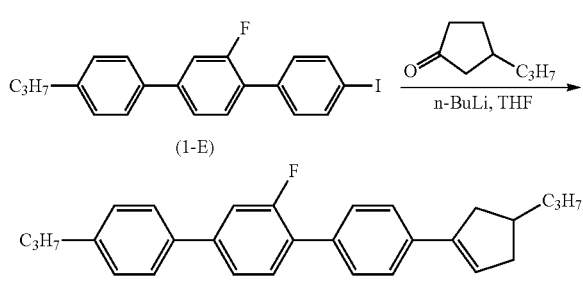

0.32 gram (0.77 millimole) of the compound (1-E) is dissolved in 5 mL of THF, and 0.34 mL (0.85 millimole) of 2.5 M n-BuLi is added at a temperature of −78° C. After the above mixture solution is stirred for 30 minutes at a temperature of −78° C., 0.097 gram (0.77 millimole) of 3-pentylcyclopentanone is added. The above mixture solution is stirred, heated to room temperature, and extracted by ethyl acetate and extracted by water. Afterwards, an organic layer of the mixture solution is desiccated by waterless magnesium sulfate and is then filtered and concentrated, and column chromatography (silicone, hexane) is performed to purify the product. The obtained initial product is added with KHSO$_4$ as a catalyst, heated to 120° C. without any solvent, and reacts for 2 hours. After the above reactant is cooled down, hexane is added to dilute the reactant, and column chromatography (silicone, hexane) is performed to purify the product. 0.18 gram of a white solid compound (3-F) is obtained. The yield is 60%.

Step 2: Synthesize the Compound in Formula (I-1) (Hereinafter "Compound (I-1)").

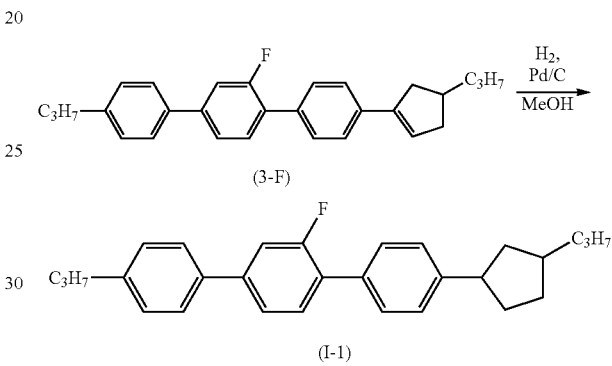

Last, 0.17 gram (0.4 millimole) of the compound (3-F) is added to 1 mL of toluene and 10 mL methanol. After 4 milligrams of 10% Pd—C is added, the above mixture solution is stirred in hydrogen for 8 hours. After aspirating a filtrate after filtration, 0.16 gram of the compound (I-1) is obtained. The yield is 94%.

Experimental Embodiment 4

Preparation of the Compound in Formula (I-3)

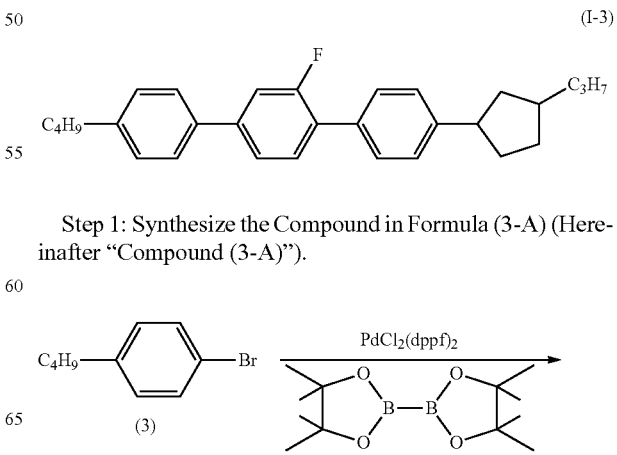

Step 1: Synthesize the Compound in Formula (3-A) (Hereinafter "Compound (3-A)").

-continued

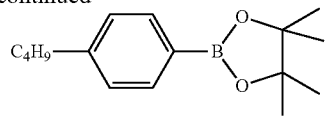

(3-A)

First, 3.2 grams (15 millimoles) of 4-bromo-1-butyl benzene in formula (3) and 4.2 grams (16.5 millimoles) of bis(pinacolate)diboron, and 4.4 grams (45 millimoles) of potassium acetate are dissolved in 30 mL of DMF. After the above mixture is stirred to a uniform state, 0.05 gram of 1,1'-bis((diphenylphosphino)ferrocene)dichloropalladium is added, and the resulting mixture is heated to 110° C. and stirred for 12 hours. After reacting, 50 mL of water is added to the mixture, and the mixture is extracted by ethyl acetate. An organic layer of the mixture solution is desiccated by waterless magnesium sulfate and is then filtered and concentrated. Afterwards, column chromatography (silicone, hexane) is performed to purify the product, thereby obtaining 3.5 grams of the compound (3-A). The yield is 90%.

Steps 2-7: Synthesize the Compound in Formula (I-3) (Hereinafter "Compound (I-3)").

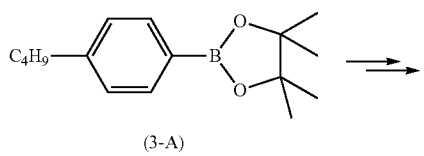

(3-A)

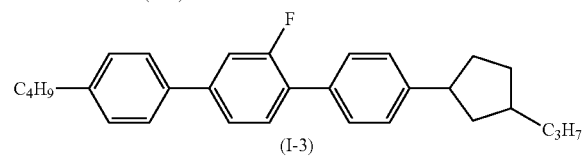

(I-3)

The conditions thereof for synthesis are the same as those in Steps 2-7 according to experimental embodiment 1.

Experimental Embodiment 5

Preparation of the Compound in Formula (I-5)

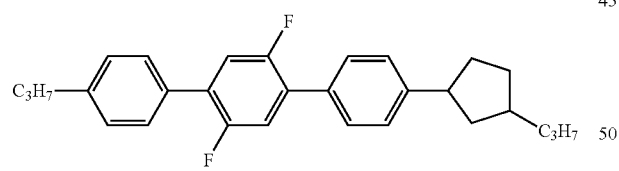

(I-5)

Step 1: Synthesize the Compound in Formula (4-B) (Hereinafter "Compound (4-B)").

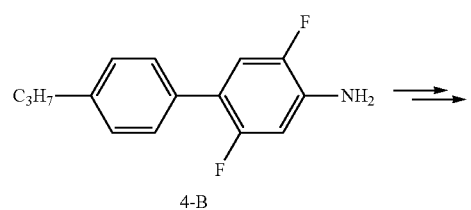

(1-A)

-continued

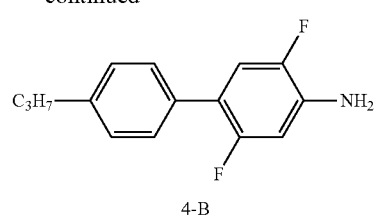

4-B 1.4 grams (5.8 millimoles) of the compound (1-A) and 1.1 grams (5.3 millimoles) of 4-bromo-2,5-fluoroaniline are dissolved in 20 mL of toluene. After the above mixture is stirred to a uniform state, 2.1 grams (15.8 millimoles) of potassium carbonate, 7 mL of water, and 0.5 mL of Aliquate™ 336 are added, and the resulting mixture reacts in an oxygen-depleted bottle for 1 hour. Then, 0.24 gram of $Pd(PPh_3)_4$ is added to the above mixture solution, and the mixture solution is heated to 85° C. and stirred for 12 hours. The above mixture solution is diluted by ethyl acetate and extracted by water. Afterwards, an organic layer of the mixture solution is desiccated by waterless magnesium sulfate and is filtered and concentrated, and column chromatography (silicone, ethyl acetate/hexane=¼) is performed to purify the product, thereby obtaining 0.91 gram of a light yellow solid compound (4-B). The yield is 70%.

Steps 2-6: Synthesize the Compound in Formula (I-5) (Hereinafter "Compound (I-5)").

4-B

3PXPCp3

The steps for synthesizing the compound (4-B) to the compound (I-5) are the same as Steps 3-7 according to experimental embodiment 1.

Comparative Embodiment 1-Comparative Embodiment 3

The following formulae (III)-(V) respectively represent chemical structures of liquid crystal compounds according to comparative embodiment 1-comparative embodiment 3. A method for synthesis according to comparative embodiment 1 and comparative embodiment 2 is the method for synthesis disclosed in U.S. Pat. No. 4,696,549, and a method for synthesis according to comparative embodiment 3 is the method for synthesis disclosed in PCT patent application publication no. WO2009100204.

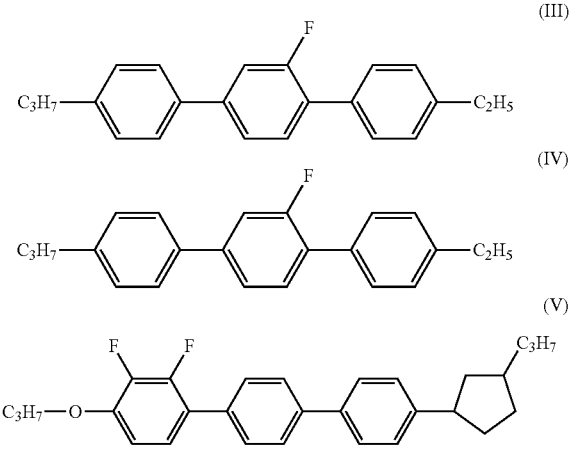

[A Method for Measuring Physical Properties of the Liquid Crystal Compounds]

Phase transformation temperatures of the compounds according to the above experimental embodiments 1-5 and comparative embodiments 1-3 are measured. The results are shown in the following Table 1.

In Table 1, a crystalline phase is denoted as C, a smectic phase is denoted as S, and a nematic phase is denoted as N. A liquid phase (isotropic) is denoted as I. In the smectic phase, in order to differentiate a smectic B phase or a smectic A phase, they are respectively denoted as $S_B$ and $S_A$. When $S_B$ and $S_A$ cannot be completed differentiated, X may be used to represent $S_B$ or $S_A$. As a notation for a phase transformation temperatures, for example, "C 40 N 130 I" means that the crystalline phase—nematic phase transformation temperature is 40° C. (meaning that a floor temperature of the nematic phase is 40° C.) and that the nematic phase—liquid phase transformation temperature is 130° C. Other notations are also noted in the same way.

(2) Nematic phase temperature intervals (ΔT) according to the above experimental embodiments 1-5 and comparative embodiments 1-3 are calculated. The results are shown in the following Table 1.

Optical anisotropy of the compounds according to the above experimental embodiments 1-5 and comparative embodiments 1-3 are measured (refractive anisotropy; measured at 25° C.; Δn). The results are shown in the following Table 1.

TABLE 1

| | PT | Δn | ΔT |
|---|---|---|---|
| Experimental embodiment 1 | C18S45N84I | 0.214 | 39 |
| Experimental embodiment 2 | C11X27X38N135I | 0.2247 | 97 |
| Experimental embodiment 3 | C40N130I | 0.2269 | 90 |
| Experimental embodiment 4 | C2S19N114I | 0.219 | 95 |
| Experimental embodiment 5 | C2N74I | 0.216 | 72 |
| Comparative embodiment 1 | C79N132I | 0.272 | 53 |

TABLE 1-continued

| | PT | Δn | ΔT |
|---|---|---|---|
| Comparative embodiment 2 | C43S63N89I | 0.254 | 26 |
| Comparative embodiment 3 | C73S111N152I | 0.184 | 41 |

According to Table 1, the liquid crystal compound according to the disclosure has a nematic phase floor temperature that is able to be lower than 45° C. and superb optical anisotropy. Moreover, the compounds according to experimental embodiments 2-5 also have high ΔT values, meaning that the liquid crystal compound according to the disclosure may be used in a wider temperature range, thereby increasing its practical value.

In light of the above, the liquid crystal compound according to the present invention has a low nematic phase floor temperature and high optical anisotropy, which are advantageous to subsequent applications and development of the liquid crystal compound.

It will be apparent to those skilled in the art that various modifications and variations can be made to the present invention without departing from the scope or spirit of the present invention. In view of the foregoing, it is intended that the present invention cover modifications and variations of this present invention provided they fall within the scope of the following claims and their equivalents.

What is claimed is:

1. A liquid crystal compound with optical anisotropy, represented by formula

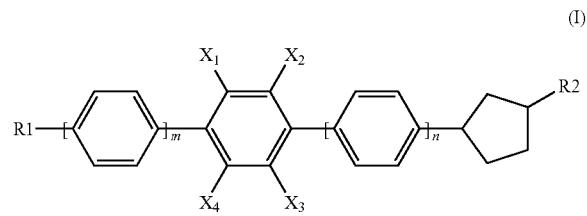

wherein each of R1 and R2 represents an alkyl group having 1 to 10 carbon atoms or an alkenyl group having 2 to 10 carbon atoms; the alkyl group and the alkenyl group are unsubstituted or substituted by —O—, —CO—, or —COO— groups; each of $X_1$, $X_2$, $X_3$, and $X_4$ represents hydrogen or fluorine, and at least one of $X_1$, $X_2$, $X_3$, and $X_4$ is fluorine; m is 1, 2, or 3; n is 0, 1, or 2, and 2≤m+n≤3.

2. The liquid crystal compound with optical anisotropy as claimed in claim 1, wherein in formula (I), $X_1$ is F, and $X_2$, $X_3$, and $X_4$ are H.

3. The liquid crystal compound with optical anisotropy as claimed in claim 1, wherein in formula (I), $X_2$ is F, and $X_1$, $X_3$, and $X_4$ are H.

4. The liquid crystal compound with optical anisotropy as claimed in claim 1, wherein in formula (I), $X_1$ and $X_3$ are F, and $X_2$ and $X_4$ are H.

5. The liquid crystal compound with optical anisotropy as claimed in claim 1, wherein in formula (I), R2 is a propyl group, a butyl group, or an amyl group.

* * * * *